United States Patent [19]

Roland et al.

[11] Patent Number: 5,503,837
[45] Date of Patent: Apr. 2, 1996

[54] CO-EXTRACTION OF AZADIRACHTIN AND NEEM OIL

[75] Inventors: Michael T. Roland, Columbia; John J. Blouin, Catonsville, both of Md.

[73] Assignee: W. R. Grace & Co.-Conn., New York, N.Y.

[21] Appl. No.: 311,379

[22] Filed: Sep. 23, 1994

Related U.S. Application Data

[62] Division of Ser. No. 36,795, Mar. 25, 1993, Pat. No. 5,397,571.

[51] Int. Cl.$^6$ ................................................. A01N 25/00
[52] U.S. Cl. ............................................. 424/405; 424/195.1
[58] Field of Search ............................. 424/405, 195.1, 424/453

[56] References Cited

U.S. PATENT DOCUMENTS

| | | | |
|---|---|---|---|
| 4,946,681 | 8/1990 | Walter | 424/195.1 |
| 5,370,873 | 12/1994 | Udeinya | 424/195.1 |
| 5,372,817 | 12/1994 | Locke | 424/405 |

*Primary Examiner*—Thurman K. Page
*Assistant Examiner*—William E. Benston
*Attorney, Agent, or Firm*—Howard J. Troffkin

[57] ABSTRACT

Disclosed is an improved method of extracting neem seeds. The method involves co-solvent extracting neem seeds with a solvent mixture of a nonpolar, aliphatic hydrocarbon solvent and a polar solvent to simultaneously remove the hydrophilic and hydrophobic extracts from the neem seeds. The method provides novel neem extract mixtures which contain both the hydrophobic and hydrophilic portion of the neem seeds. The extract mixtures may be further extracted to yield an azadirachtin-containing solid product having greater than 10 weight percent of azadirachtin.

21 Claims, No Drawings

CO-EXTRACTION OF AZADIRACHTIN AND NEEM OIL

This is a division of application Ser. No. 08/036,795, filed Mar. 25, 1993 now U.S. Pat. No 5,397,571.

FIELD OF THE INVENTION

This invention relates to a novel process for the solvent extraction of neem seeds. More specifically, this invention relates to a novel process for extracting neem seeds to simultaneously co-extract the hydrophobic and hydrophilic portions of the seeds. This invention also relates to novel neem seed products prepared by the process of this invention.

BACKGROUND OF THE INVENTION

The neem tree, a tropical evergreen, has been used for centuries as a source of pesticides to which insects have not developed a resistance. Various neem seed extracts, particularly the ones containing the tetranortriterpenoid azadirachtin, are known to influence the feeding behavior, metamorphosis (insect growth regulating effect), fecundity, and fitness of numerous insect and fungal species belonging to various orders.

Neem seeds also contain various oily substances, at least one of which has been used for its medicinal and therapeutic properties for centuries. However, oils have been produced from neem seeds by a number of methods. This has lead to a great variability in the properties of neem oils. Very little chemical characterization has therefore been possible. Many of the publications referring to oils isolated from need seeds give no information as to its preparation, which is the key determinant of its composition.

There are two principle methods of obtaining extracts from neem seeds: expulsion, where the extract is pressed from the seeds, and extraction, where the extract is removed from the seeds by solubilization in a solvent. Inherently, materials made by these methods have very different properties. Extracts expelled from the seed will also contain water expelled from the seed by the same process. This aqueous material will carry along with it liminoids, such as azadirachtin, which themselves have pesticidal activity.

There are various methods known in the prior art to extract azadirachtin from neem seeds, including the use of solvents such as methanol, ethanol, water, methylene chloride, chloroform, hexane, methylethylketone, butanol, petroleum benzene, ether, acetone, methyl tertbutyl ether, diethylcarbonate, etc. In general, there have been two methods use to solvent extract materials from neem seeds. In one method, the neem seeds were ground and hydrophobic fatty acids and oils were removed by extraction of the seeds with a nonpolar solvent. The ground seeds are then extracted with a hydrophilic polar solvent to remove the hydrophilic, azadirachtin-containing neem fractions from the neem seeds. In a second prior art method, the neem seeds were first extracted with a polar solvent to remove the hydrophilic azadirachtin-containing fraction from the seeds. The hydrophilic residue was then extracted with a nonpolar solvent to remove residual hydrophobic fatty acid and oils.

Disadvantages often associated with prior art method heretofore used to extract azadirachtin from neem seeds include (1) the need to dry the seeds in a very temperature sensitive state; (2) cross-contamination of polar and nonpolar solvent streams; (3) water accumulation in the polar solvent streams; (4) co-extraction of very polar components, such as carbohydrates, which complicates downstream processing the extract; (5) low azadirachtin concentrations or yields in the extract product; and (6) low oil recovery yields.

SUMMARY OF THE INVENTION

It has now been discovered that problems heretofore associated with conventional methods used for solvent extracting neem seeds can be diminished or eliminated by co-solvent extracting of neem seeds with a mixture of a nonpolar, aliphatic hydrocarbon solvent and a polar solvent to simultaneously remove the hydrophilic and hydrophobic extracts from the seeds in a single extraction step. The co-extraction process of the invention provides a narrow polarity range of extraction which diminishes the extraction of highly polar materials, i.e., as carbohydrates and water, thereby improving downstream processing of the neem extracts and providing an azadirachtin-containing product having higher concentrations of azadirachtin than typically obtained in prior extraction processes. The process of the invention also avoids cross-contamination problems associated with prior art extraction techniques using separate polar and nonpolar solvent streams, and eliminates the need to dry the neem seeds between extractions while the seeds are in a temperature-sensitive state.

Accordingly, it is an object of this invention to provide an improved process for the solvent extraction of neem seeds, which process eliminates or diminishes problems associated with solvent extraction techniques heretofore used to obtain extracts from neem seeds.

It is another object of this invention to provide a novel process of solvent extracting neem seeds, which process involves simultaneously extracting the hydrophilic, azadirachtin-containing portion of the neem seeds and the hydrophobic, neem oil portion of the seeds in a single extraction step.

Another object of this invention is to provide a novel neem extract which contains both the hydrophilic, azadirachtin-containing portion and the hydrophobic, neem oil portion of the seeds.

It is another object of this invention to provide a novel azadirachtin-containing, solid neem product having an increased concentration of azadirachtin.

DETAILED DESCRIPTION OF THE INVENTION

The present invention is directed to a novel process of solvent extracting neem seeds to obtain pesticidal neem extracts. The process involves extracting ground neem seeds with a co-solvent mixture of a nonpolar, aliphatic hydrocarbon solvent and a polar solvent for a time period and at a temperature sufficient to obtain a neem extract having both the hydrophilic azadirachtin-containing portion and the hydrophobic neem oil portion of the seeds. The extraction process of the invention may be performed at a temperature of about 25° C. up to the boiling temperature of the co/solvent extraction. Preferably, the extraction is accomplished at a temperature of about 40° C. to about 60° C. The extraction is performed for a period of time sufficient to obtain optimum extraction of the neem seeds. Preferably, the extraction process is carried out for about 2 to about 12 hours. If desired, the co-extraction process maybe repeated to optimize the extraction efficiency. Following extraction, the co-solvent neem extract is treated to separate the hydrophilic and hydrophobic portions of the extract.

The extraction process of the invention can be accomplished using various combinations of a nonpolar, aliphatic hydrocarbon solvent and a polar solvent. For purposes of this invention, nonpolar, aliphatic hydrocarbons include those aliphatic hydrocarbons having high neem oil solubility and substantially no azadirachtin or water solubility. Suitable aliphatic hydrocarbons include, but are not limited to, aliphatic hydrocarbons and halogenated aliphatic hydrocarbons having from 1 to 20, preferably 1 to 10 carbon atoms, i.e. pentane, hexane, heptane, octane, nonane, decane, isooctane, chloropentane, chlorohexane, and the like, and their isomers; petroleum distillates, petroleum ether, and the like, and mixtures thereof. Various other nonpolar aliphatic hydrocarbons having the above characteristics are well known to those skilled in the art, and the choice of a particular solvent is not per se critical to the invention, provided that it is substantially azadirachtin-insoluble and neem oil has a high degree of solubility therein. Preferably, the nonpolar polar aliphatic hydrocarbon solvent is miscible with the polar solvent of choice to form a substantially homogenous solution.

Polar solvents useful in the co-extract process of the invention include any polar solvent which has a high degree of azadirachtin solubility. Preferably, the polar solvent is miscible with the non-polar solvent to form a substantially homogeneous solution. Suitable polar solvents include, but are not limited to, aliphatic alcohols, ketones, nitriles, substituted aromatic, such as alkyl or halogenated aromatics, amides sulfoxides, alkyl carbonates, chlorinated aliphatics, aromatic aldehydes, sulfones, ethers, esters, and the like, or mixtures thereof. Preferred polar solvents for use in the present invention include, but are not limited to, aliphatic alcohols such as methanol, ethanol, propanol, isopropanol, butanol, 2-butanol, t-butanol, benzyl alcohol, and the like, and mixtures thereof.

For purposes of this invention, the term alkyl as used herein refers to alkyl groups having from 1–10, preferably 1 to 6 carbon atoms.

The concentration of aliphatic hydrocarbon and polar solvents useful in the co-extraction process will vary. In general, the nonpolar, aliphatic hydrocarbon and polar solvents should be present in the solvent mixture in an amount sufficient to permit extraction of both the hydrophilic and hydrophobic components desired from the neem seeds. Suitable solvent mixtures useful in the present invention may include about 10 to about 90 weight percent of the nonpolar, aliphatic hydrocarbon solvent and about 90 to about 10 weight percent of the polar solvent. Preferably, the solvent mixtures useful in the invention include about 40 to about 70 weight percent of the nonpolar, aliphatic hydrocarbon solvent and about 30 to about 60 weight percent of the polar solvent; most preferably about 60 weight percent of the nonpolar, aliphatic hydrocarbon solvent and about 40 weight percent of the polar solvent.

Separation of the hydrophilic and hydrophobic portions of the solvent extract mixture is carried out by means known to one skilled in the arts. In a preferred embodiment, a counter-extraction process is used. In the counter-extraction process the co-solvent neem extract is stripped of solvent to recover the "neem extract mixture". For purposes of the invention, the term "neem extract mixture" is used to designate a neem extract containing both the hydrophilic, azadirachtin-containing portion of the neem seeds and the hydrophobic neem oil portion of the seeds from which substantially all of the extraction co-solvent has been removed. The neem extract mixture is thereafter contacted with a solvent having a sufficiently low polarity, i.e., hexane, to precipitate as a solid the hydrophilic, azadirachtin-containing portion of the extract. The solid is recovered by known techniques, e.g., filtration. The azadirachtin-containing solid formed by this method contains high concentrations of azadirachtin, i.e., greater than 10 weight percent, preferably greater than 15 weight percent, most preferable greater than 20 weight percent, of azadirachtin. The remaining hydrophobic neem oil portion of the extract mixture is recovered from the filtrate by removing the solvent.

In an alternative embodiment, a combination separation and dewaxing step may be used to separate the hydrophilic and hydrophobic portions of the co-solvent extract mixture. In this procedure, the co-solvent extract mixture is chilled at a temperature sufficient to phase split the extract mixture into oil-rich and oil-lean phases. The temperature will vary depending upon the level of hydrophobic solvent in the co-solvent neem extract. Preferably, the co-solvent extract mixture is chilled at a temperature of about 5° C. or lower. The oil-lean upper phase will contain substantially all of the hydrophilic azadirachtin-containing fraction and the oil-rich phase will contain the hydrophobic neem oil fraction. Separate azadirachtin-containing and neem oil fractions are recovered by independently removing solvents from these phases to obtain two liquid neem products, respectively. In addition, under chilled conditions a third wax phase may form, depending upon the temperature and the level of the hydrophobic solvent used in the co-solvent extraction. This wax phase may be independently recovered by filtration.

In a variation of this embodiment, the co-solvent extract mixture may be treated to remove the solvent to obtain the neem extract mixture. The mixture is then combined with a solvent having a sufficiently high polarity, e.g., alcohol or alcohol/water mixtures, to produce phase-splitting in the resulting solvent mixture. Using this approach, phase splitting similar to that as described hereinabove can be achieved at room temperature, but is further enhanced under chilled conditions, i.e., temperature of about 10° C. or lower. Again, a third wax phase may form which can be recovered by filtration. Separate hydrophilic, azadirachtin-containing and hydrophobic neem oil fractions may be recovered by independently removing the solvent from these phases to yield liquid product phases and a wax waste stream.

Without further elaboration, it is believed that one skilled in the art, using the preceding detailed description can utilize the present invention to its fullest extent.

The following examples are provided to illustrate the invention in accordance with the principles of this invention, but are not to be construed as limiting the invention in any way except as indicated in the appended claims. All parts and percentages are by weight unless otherwise indicated.

EXAMPLE 1

The following were combined in a 3 liter jacketed glass reactor:

635 grams ethanol
275 grams hexane
603 grams dehulled, ground neem seeds

The above slurry was mixed for ~10 hours at 55° C. The slurry was then centrifuged to recover 666 grams of extract and 589 grams of "wet" seeds. The extract was stripped of solvents under vacuum at 55° C. resulting in 156 grams of oil extract at ~0.9 wt % azadirachtin. The extract was combined with 654 grams of hexane (including washes) which resulted in the formation of a solid precipitate dispersed in the oil/hexane phase. The precipitate was recovered by filtration, resulting in ~5 grams of solid extract containing about 23 wt % azadirachtin. The hexane was stripped to recover 166 grams of neem oil.

EXAMPLE 2

The following were combined in a 3 liter jacketed glass reactor:

1046 grams ethanol 451 grams hexane 1007 grams dehulled, ground neem seeds

The above slurry was mixed for ~10 hours at 55° C. The slurry was then centrifuged and the seeds washed with 350 grams solvent containing 70% ethanol and the remainder hexane. A total of 1565 grams of extract and 906 grams of "wet" seeds were recovered. The extract was then recycled back to the reactor as follows:

1537 grams of above extract 1018 grams dehulled, ground seeds

The slurry was again mixed for ~10 hours at 55° C. The slurry was centrifuged and the seeds washed with 250 grams solvent containing 70% ethanol and the remainder hexane. 1472 total grams of extract and 1028 grams of "wet" seeds were recovered. This extract was stripped of solvent under vacuum at 55° C. resulting in 561 grams of oily extract at ~0.9 wt % azadirachtin. The extract was combined with 1989 grams hexane (including washes) which resulted in the formation of a solid precipitate dispersed in the oil/hexane phase. The precipitate was recovered by filtration, resulting in ~17 grams of solid extract containing 23 wt % azadirachtin. The hexane was stripped to recover 637 grams of oil.

What is claimed is:

1. An improved process for solvent extracting neem seeds comprising contacting neem seeds with a co-solvent mixture of a nonpolar, aliphatic hydrocarbon solvent and a polar solvent to simultaneously remove the hydrophilic, azadirachtin-containing fraction and the hydrophobic, neem oil-containing fraction of the seeds.

2. The process of claim 1 wherein the co-solvent mixture comprise from about 10 to about 90 weight percent of the aliphatic hydrocarbon solvent and from about 90 to about 10 weight percent of the polar solvent.

3. The process of claim 2 wherein the co-solvent mixture comprise from about 60 weight percent of the aliphatic hydrocarbon solvent and about 40 weight percent of the polar solvent.

4. The process of claim 1 wherein the nonpolar, aliphatic hydrocarbon solvent is pentane, hexane, heptane, octane, nonane, decane, isoctane, chloropentane, chlorohexane, isomers thereof, petroleum distillates, petroleum ether, or mixtures thereof.

5. The process of claim 1 wherein the polar solvent is selected from the group consisting of methanol, ethanol, propanol, isopropanol, butanol, 2-butanol, t-butanol, benzyl alcohol and mixtures thereof.

6. The process of claim 1 wherein the polar solvent is ethanol and the aliphatic hydrocarbon solvent is hexane.

7. The process of claim 1 wherein the polar solvent and aliphatic hydrocarbon solvent of the co-solvent mixture are miscible and form a substantially homogenous co-solvent mixture.

8. A process for preparing a neem extract mixture from neem seeds which extract mixture contains the hydrophilic, ,azadirachtin-containing portion of the seeds and the hydrophobic, neem oil-containing portion of the seeds, said process comprising a. contacting neem seeds with a co-solvent mixture of a polar solvent and a nonpolar, aliphatic hydrocarbon solvent for a period of time sufficient to obtain a co-solvent neem extract;

b. removing the solvent from the co-solvent neem extract; and c. recovering said neem extract mixture.

9. The process of claim 8 wherein the aliphatic hydrocarbon solvent is pentane, hexane, heptane, octane, nonane, decane, isoctane, chloropentane, chlorohexane, isomers thereof, petroleum distillates, petroleum ether, or mixtures thereof.

10. The process of claim 8 wherein the polar solvent is methanol, ethanol, propanol, isopropanol, butanol, 2-butanol, t-butanol, benzyl alcohol or mixtures thereof.

11. The process of claim 8 wherein the polar solvent and aliphatic hydrocarbon solvent of the co-solvent mixture are miscible and form a homogeneous co-solvent mixture.

12. A neem extract mixture produced by the process of claim 8.

13. An improved extraction process of obtaining neem oil and azadirachtin from neem seeds comprising (a) contacting neem seeds with a co-solvent mixture of a polar solvent and a nonpolar, aliphatic hydrocarbon solvent for a period of time sufficient to obtain a co-solvent neem extract having the hydrophilic, azadirachtin-containing portion of the seeds and the hydrophobic, neem oil portion of the seeds; and (b) treating the co-solvent neem extract to separate and independently recover the hydrophilic, azadirachtin-containing portion and the hydrophobic, neem oil portion of the co-solvent neem extract.

14. A method of claim 13 wherein the co-solvent neem extract in step (b) is treated by (c) removing the solvent from the co-solvent neem extract to recover a neem extract mixture;

(d) contacting the neem extract mixture with a solvent having a sufficiently low polarity to precipitate an azadirachtin-containing neem solid and dissolve the neem oil;

(e) separating and recovering the azadirachtin-containing neem solid from the solvent; and (f) removing the solvent to recover the neem oil.

15. A method of claim 13 wherein the co-solvent neem extract in step (b) is treated by (g) removing the solvent from the co-solvent neem extract to recover a neem extract mixture;

(h) contacting the neem extract mixture with a solvent having a sufficiently high polarity to form an oil-lean, azadirachtin-containing upper phase and an oil-rich, neem oil-containing lower phase;

(i) separating the oil-lean phase and oil-rich phase;

(j) removing the solvent from the oil-lean phase to recover an azadirachtin-containing neem product; and (k) removing the solvent from the oil-rich phase to recover the neem oil.

16. The method of claim 15 wherein the neem extract mixture is contacted with the high polarity solvent at a temperature of about 10° C. or lower.

17. A method of claim 13 wherein the co-solvent neem extract in step (b) is treated by (1) chilling the co-solvent neem extract at a temperature sufficient to form an oil-lean, azadirachtin-containing upper phase and an oil-rich, neem oil containing lower phase;

(m) separating the oil-lean phase and oil-rich phase;

(n) removing the solvent from the oil-lean phase to recover an azadirachtin-containing neem product; and (o) removing the solvent from the oil-rich phase to recover neem oil.

18. The method of claim 17 wherein the co-solvent neem extract is chilled at a temperature of about 5° C. or lower.

19. An improved process for solvent extracting neem seeds comprising contacting neem seeds with a co-solvent mixture of a nonpolar, aliphatic hydrocarbon solvent and a polar solvent to simultaneously remove the hydrophilic, azadirachtin-containing fraction and the hydrophobic, neem oil-containing fraction of the seeds, wherein the azadirachtin-containing fraction is effectively extracted without requiring the neem seeds to be dried when the seeds are in a temperature sensitive state.

20. A process for preparing a neem extract mixture from neem seeds which extract mixture contains the hydrophilic, azadirachtin-containing portion of the seeds, said process comprising a. contacting neem seeds with a co-solvent mixture of a polar solvent and a nonpolar, aliphatic hydrocarbon solvent for a period of time sufficient to obtain a co-solvent neem extract;

b. removing the solvent from the co-solvent neem extract; and c. recovering said neem extract mixture without requiring the neem seeds to be dried when the seeds are in a temperature sensitive state.

21. An improved extraction process of obtaining neem oil and azadirachtin from neem seeds comprising (a) contacting neem seeds with a co-solvent mixture of a polar solvent and a nonpolar, aliphatic hydrocarbon solvent for a period of time sufficient to obtain a co-solvent neem extract having the hydrophilic, azadirachtin-containing portion of the seeds and the hydrophobic, neem oil portion of the seeds; and (b) treating the co-solvent neem extract to separate and independently recover the hydrophilic, azadirachtin containing portion and the hydrophobic, neem oil portion of the co-solvent neem extract, wherein the azadirachtin-containing portion is effectively extracted without requiring the neem seeds to be dried when the seeds are in a temperature sensitive state.

* * * * *